United States Patent [19]

Woodward et al.

[11] Patent Number: 4,525,187
[45] Date of Patent: Jun. 25, 1985

[54] DUAL DEPHLEGMATOR PROCESS TO SEPARATE AND PURIFY SYNGAS MIXTURES

[75] Inventors: Donald W. Woodward, New Tripoli; Arthur T. Katsaros, Bethlehem; Howard C. Rowles, Center Valley, all of Pa.

[73] Assignee: Air Products and Chemicals, Inc., Allentown, Pa.

[21] Appl. No.: 579,845

[22] Filed: Jul. 12, 1984

[51] Int. Cl.³ ............................................... F25J 3/02
[52] U.S. Cl. ............................................ 62/31; 62/34
[58] Field of Search ................... 62/9, 11, 23, 24, 27, 62/28, 31, 32, 34

[56] References Cited

U.S. PATENT DOCUMENTS

| | | |
|---|---|---|
| 3,315,475 | 4/1967 | Harmens . |
| 3,633,371 | 1/1972 | Davison . |
| 3,886,756 | 1/1975 | Allam et al. . |
| 4,102,659 | 7/1978 | Martin . |
| 4,252,548 | 2/1981 | Markbreiter et al. . |
| 4,270,939 | 6/1981 | Rowles et al. . |
| 4,338,107 | 7/1982 | Swallow . |
| 4,443,238 | 4/1984 | Beddome et al. ...................... 62/21 |

*Primary Examiner*—Frank Sever
*Attorney, Agent, or Firm*—Mark L. Rodgers; James C. Simmons; E. Eugene Innis

[57] ABSTRACT

The present invention involves a process for separating and purifying gas mixtures comprising $H_2$, CO and $C_1+$ hydrocarbons. The gas is initially cooled in a high pressure dephlegmator to condense and rectify the $C_1+$ hydrocarbons leaving a combined $H_2$—CO vapor. The condensed $C_1+$ hydrocarbons are partially vaporized and subsequently recondensed in a second, low pressure dephlegmator with further rectification. This process yields $H_2$—CO vapor streams and a $C_1+$ liquid hydrocarbon product at purities suitable for subsequent commercial operations.

24 Claims, 1 Drawing Figure

DUAL DEPHLEGMATOR PROCESS TO SEPARATE AND PURIFY SYNGAS MIXTURES

TECHNICAL FIELD

The present invention relates to a process for separating and purifying gas mixtures comprising $H_2$, CO, and $C_1+$ hydrocarbons. One particular embodiment involves the recovery of components from multicomponent syngas mixtures derived as off-gas in industrial processes.

BACKGROUND OF THE INVENTION

A typical syngas mixture produced, for example, by coal gasification or partial oxidation, typically contains $H_2$, CO and $C_1$ and heavier hydrocarbons. Previously, treatment of syngas mixtures has been directed toward separating high volatile components, such as hydrogen, from low volatile components, such as carbon monoxide. This separation was achieved using several condensation, absorption and vaporization steps. The hydrocarbons present in the syngas, primarily methane, were used as a wash liquid to effect essentially complete separation of $H_2$ and CO. The resulting CO—$C_1+$ hydrocarbon mixture was then separated at low pressure by conventional distillation techniques. Such processes are described in U.S. Pat. Nos. 4,102,659 and 4,338,107.

Alternatively, CO and $C_1+$ hydrocarbons were separated from the $H_2$ by means of one or more partial condensation steps, followed again by conventional distillation at low pressure to separate the CO—$C_1+$ hydrocarbon mixture. One such process is described in U.S. Pat. No. 4,217,759.

U.S. Pat. No. 4,270,939 discloses a process whereby separate hydrogen, nitrogen and/or carbon monoxide, and methane product streams are recovered. Separation is obtained by effecting condensation of at least a major portion of the methane content in a dephlegmator wherein separate lower boiling components are employed as indirect heat exchange refrigerants. The methane is then recovered as a low purity product stream. $H_2$ and $N_2$/CO are further separated via a conventional partial condensation step and subsequently recovered as separate pure gas streams.

BRIEF SUMMARY OF THE INVENTION

A new process has been developed for separating a high pressure feed gas comprising $H_2$, CO, and $C_1+$ hydrocarbons into $H_2$—CO product streams and a $C_1+$ hydrocarbon product. This new process comprises cooling the high pressure feed gas by indirect heat exchange in a high pressure dephlegmator by passing the feed gas in a generally upward direction through the dephlegmator. This cooling with attendant rectification causes essentially all of the $C_1+$ hydrocarbons to condense with minimal condensation of CO, thereby forming a separate high pressure $H_2$—CO vapor stream and a high pressure $C_1+$ enriched liquid stream. The high pressure $C_1+$ enriched liquid stream is then expanded to a lower pressure and subsequently partially vaporized to form a low pressure vapor stream and a low pressure $C_1+$ liquid product. The low pressure vapor stream is cooled in a low pressure dephlegmator using the high pressure $H_2$—CO vapor stream from the high pressure dephlegmator as an indirect heat exchange refrigerant in countercurrent flow to the low pressure vapor stream. Cooling in the low pressure dephlegmator with further rectification causes essentially all of the $C_1+$ hydrocarbons to recondense, again with minimal condensation of CO, thereby producing a separate low pressure $H_2$—CO vapor stream and additional low pressure $C_1+$ liquid product. The separate high pressure $H_2$—CO vapor stream, low pressure $H_2$—CO vapor stream and low pressure $C_1+$ liquid product are then recovered.

This process provides for the efficient recovery of product $H_2$—CO mixtures at a purity of less than 1 mole % of $C_1$ and higher hydrocarbons. This level of purity is desirable if the $H_2$—CO mixtures are to be used for further operations such as methanol or oxo-alcohol production. Also, this process allows for the recovery of high-quality $C_1+$ fuel which complies with pipeline specifications for such gases.

This process is more efficient for $H_2$—CO syngas purification than the prior art processes because it minimizes the quantity of CO which is condensed in the high pressure stage and subsequently separated from the $C_1+$ hydrocarbons. Therefore, more of the CO is recovered at high pressure, resulting in reduced refrigeration load, a reduced quantity of CO to be separated from the $C_1+$ hydrocarbons in the low pressure separation stage, and reduced CO recompression. Similarly, less CO is recondensed in the low pressure separation stage, which further reduces refrigeration requirements, particularly where high CO recovery and high $C_1+$ hydrocarbon purity are essential.

An additional advantage of the present process is that, previously, coal gasification facilities designed to produce methanol normally included a shift reactor to increase the ratio of $H_2$ to CO in the feed gas to the stoichiometric value required for the optimum production of methanol. The present process eliminates the need for this reactor and its associated heat exchange equipment because it yields two separate $H_2$—CO products that can be blended to produce the desired product composition.

DETAILED DESCRIPTION OF THE INVENTION

Figure 1:
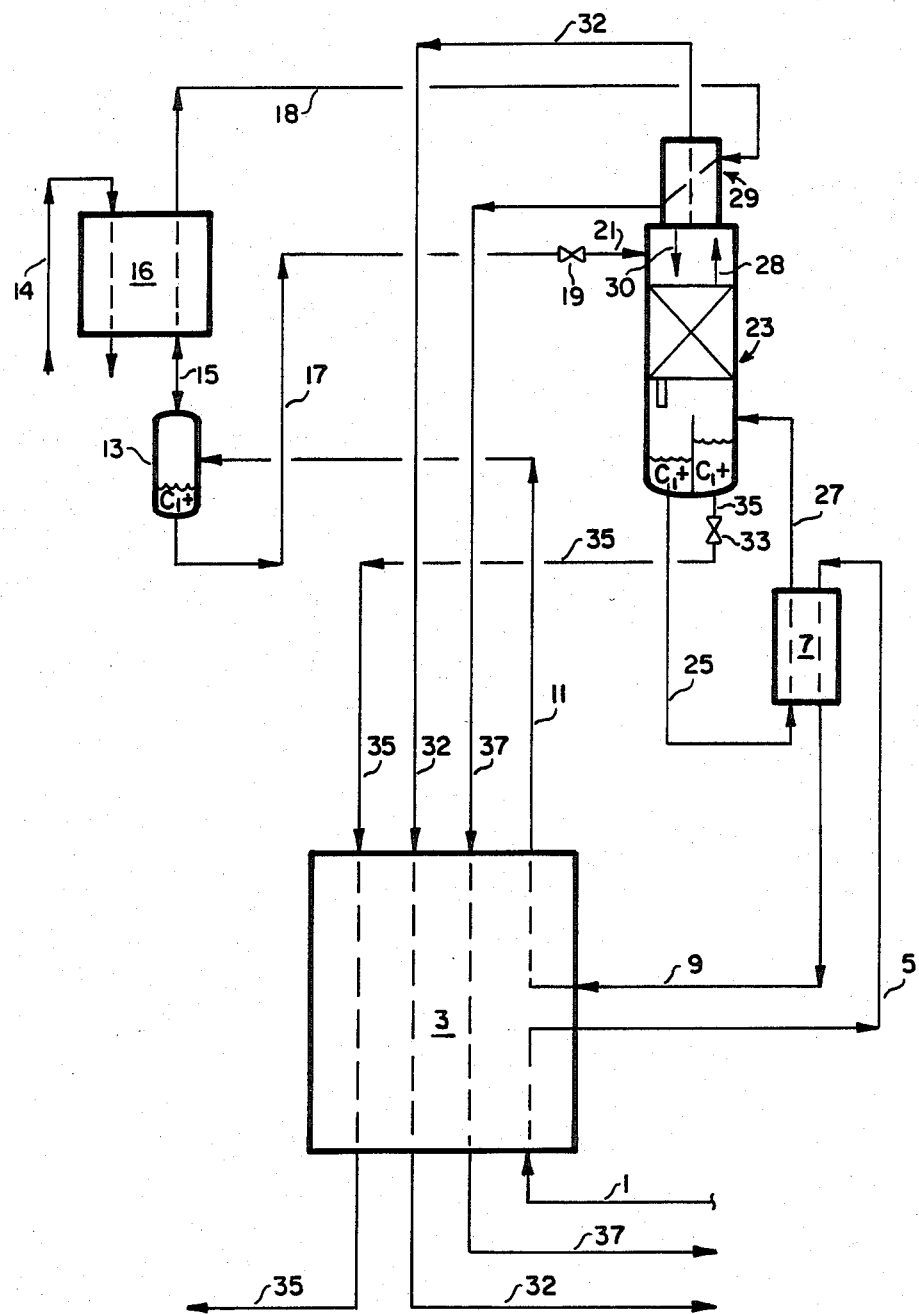
FIG. 1 is a schematic flow diagram of a separation and recovery system according to one embodiment of the invention.

Referring to FIG. 1, a high pressure feed gas 1 comprised of $H_2$, CO and $C_1+$ hydrocarbons is cooled to near its dew point against effluent $H_2$—CO product streams 32 and 37 in a feed cooler 3. This feed gas stream 1 is typically a syngas mixture from a plant such as a coal gasification plant, although any gas with the composition described above can be treated by this process. Generally the feed gas 1 enters the system at a pressure of about 20 to 70 atmospheres, although a wider pressure range can be tolerated. The feed gas 1 may be also passed through a reboiler 7 to be used as a heat source for indirect heat exchange in the reboiler 7. Alternatively, an external heat source, such as a closed loop $N_2$ recycle stream, may be used as a heat source for reboiler 7.

The cooled high pressure feed gas 11 is then passed upwardly through a feed separator 13 and a high pressure dephlegmator 16 wherein the feed gas is cooled to a temperature of between about $-150°$ to $-190°$ C. This cooling with attendant rectification effects condensation of essentially all of the $C_1+$ hydrocarbons, thereby producing a high pressure $H_2$—CO vapor stream 18 and a high pressure $C_1+$ enriched liquid hydrocarbon stream 17. As it condenses, the high pressure $C_1+$ hydrocarbon stream flows downward as a reflux liquid countercurrent to the high pressure feed gas flowing upward in dephlegmator 16. Thus, interaction takes place between the upward flowing vapor and the downward flowing liquid. Rectification results, wherein the gaseous mixture 18 discharged overhead from the dephlegmator 16 is enriched in CO while the liquid leaving the dephlegmator through line 15 is enriched in $C_1+$ hydrocarbons. The concentration of CO in the high pressure $C_1+$ enriched liquid stream 17 is thereby minimized by the fractionation achieved in the high pressure dephlegmator 16.

Refrigeration for the high pressure dephlegmator 16, depicted by stream 14, can be provided by any conventional and effective means, such as by a closed loop $N_2$ recycle system or by work expansion of the product $H_2$—CO streams.

The high pressure $H_2$—CO vapor 18, containing less than about 1 mole % $C_1+$ hydrocarbons, exits the top of the high pressure dephlegmator 16. The high pressure $C_1+$ enriched hydrocarbon liquid containing some $H_2$—CO impurities is collected in feed separator 13.

High pressure $C_1+$ enriched liquid hydrocarbon stream 17 exits the feed separator 13 and is subsequently passed through expansion valve 19 where it is expanded to between about 5 to 20 atmospheres forming a low pressure $C_1+$ enriched liquid hydrocarbon stream in line 21. This $C_1+$ enriched liquid hydrocarbon stream flows downward in CO—$C_1+$ splitter column 23 and is heated in reboiler 7 to effect partial vaporization forming a low pressure vapor stream and a low pressure $C_1+$ liquid hydrocarbon product in line 27. The low pressure vapor stream may be passed upward in CO—$C_1+$ splitter column 23 through conventional trays or packing to strip CO from the downward flowing liquid. The low pressure vapor stream 28, enriched with CO, is passed through a low pressure dephlegmator 29 positioned above the upper portion of splitter column 23. In low pressure dephlegmator 29 the low pressure CO enriched vapor stream 28 is cooled to a temperature of between about $-145°$ to $-185°$ C. and further rectified using the high pressure $H_2$—CO vapor stream 18 from the high pressure dephlegmator 16 as an indirect heat exchange refrigerant in countercurrent flow.

This cooling effects recondensation of essentially all of the $C_1+$ hydrocarbons which flow downward as a reflux liquid countercurrent to the upward flowing vapor in low pressure dephlegmator 29. Again, interaction takes place between the upward flowing vapor and the downward flowing liquid. Rectification results, wherein the gaseous mixture 32 discharged overhead from the low pressure dephlegmator 29 is further enriched in CO and the liquid stream 30 leaving the bottom of the low pressure dephlegmator 29 is enriched in $C_1+$ hydrocarbons.

The $C_1+$ enriched liquid stream 30 leaving the bottom of the low pressure dephlegmator 29 can be recovered as additional low pressure $C_1+$ liquid product or optionally mixed with the $C_1+$ enriched liquid stream entering the splitter column 23 via line 21, which flows downward through the column for removal of residual CO. As a result, essentially all of the $C_1+$ hydrocarbons are condensed and collected at low pressure in the bottom of splitter column 23, and a low pressure $H_2$—CO vapor stream 32, containing less than about 1 mole % $C_1+$ hydrocarbons, exits at the top of low pressure dephlegmator 29. As described above, the CO—$C_1+$ splitter column 23 consists of, at least, a reboiler 7 for partial vaporization of the $C_1+$ enriched hydrocarbon liquid stream, and may also contain trays and/or packing to increase the purity of the $C_1+$ liquid hydrocarbon product if necessary.

The low pressure $C_1+$ liquid hydrocarbon product collected in splitter column 23 is recovered as stream 35, while the separate low and high pressure $H_2$—CO vapor streams, 32 and 37 respectively, are also recovered. If desired, the pressure of the liquid $C_1+$ product stream 35 can be regulated, for example, for refrigeration purposes, via valve 33 prior to final recovery. Both the low and high pressure $H_2$—CO vapor streams 32 and 37 can be used, prior to recovery, as refrigerants for cooling the high pressure feed gas 1 in feed cooler 3.

Several designs were carried out in accordance with the preferred embodiment described above, and are described in more detail in Examples 1 and 2 below. These examples are illustrative of the claimed invention and are not meant to be limiting.

EXAMPLE 1

A syngas mixture containing about 54.4 mole % $H_2$, 28.2 mole % CO, 17.0 mole % $C_1+$ hydrocarbons and 0.4 mole % $N_2$ is treated by the present process. The material balance for this process is reported in Table 1 below. The stream numbers refer to the points as represented in FIG. 1.

TABLE 1

| Stream number | 1 | 11 | 17 | 18 | 21 | 25 | 27 | 32 | 35 | 37 |
|---|---|---|---|---|---|---|---|---|---|---|
| Pressure (atm) | 27.2 | 26.9 | 26.9 | 26.9 | 15.8 | 15.9 | 15.9 | 15.6 | 15.9 | 26.5 |
| Temperature (°C.) | −23 | −143 | −148 | −172 | −149 | −111 | −110 | −157 | −110 | −146 |
| Flow Rates (Moles/hr.) (Vapor) | | | | | | | | | | |
| Hydrogen | 15,884 | 15,852 | — | 15,700 | 114 | — | — | 184 | — | 15,700 |
| Carbon Monoxide | 8,238 | 7,956 | — | 6,257 | 122 | — | 19 | 1,976 | — | 6,257 |
| $C_1+$ Hydrocarbons | 4,953 | 3,535 | — | 111 | 39 | — | 4,995 | 14 | — | 111 |
| Nitrogen | 127 | 123 | — | 105 | 2 | — | — | 22 | — | 105 |
| TOTAL | 29,202 | 27,466 | — | 22,173 | 277 | — | 5,014 | 2,196 | — | 22,173 |
| Flow Rate (Moles/hr.) (Liquid) | | | | | | | | | | |
| Hydrogen | — | 32 | 184 | — | 70 | — | — | — | — | — |
| Carbon Monoxide | — | 282 | 1,981 | — | 1,859 | 24 | 5 | — | 5 | — |
| $C_1+$ Hydrocarbons | — | 1,418 | 4,842 | — | 4,803 | 9,823 | 4,828 | — | 4,828 | — |
| Nitrogen | — | 4 | 22 | — | 20 | — | — | — | — | — |
| TOTAL | — | 1,736 | 7,029 | — | 6,752 | 9,847 | 4,833 | — | 4,833 | — |

Feed stream 1, at −23° C. and 27.2 atm, is cooled to −143° and partially condensed in feed cooler 3. The resulting vapor-liquid stream 11 is separated in feed separator 13. The uncondensed vapor is further cooled to −172° C. in high pressure dephlegmator 16, wherein condensed liquid flows downward countercurrent to and interactive with the upward flowing vapor. As a result of the rectification achieved in the high pressure dephlegmator 16, the resulting liquid stream 17 exiting feed separator 13 at −148° C. and 26.9 atm is enriched to a concentration of about 69 mole % $C_1+$ hydrocarbons. The high pressure $H_2$—CO gaseous product stream 18 discharged overhead from the high pressure dephlegmator 16 contains only 0.5 mole % $C_1+$ hydrocarbons.

The high pressure $C_1+$ enriched liquid hydrocarbon stream 17 is expanded via valve 19 to 15.8 atm and −149° C., and enters the CO—$C_1+$ splitter column 23 via line 21. The liquid flows down the column through trays or packing and enters the reboiler 7 at 15.9 atm and −111° C. The liquid $C_1+$ enriched stream 25 is partially vaporized in reboiler 7 and the resulting vapor-liquid stream in line 27 at 15.9 atm and −110° C. is separated to provide vapor flow for the column 23 and a high purity, low pressure liquid $C_1+$ hydrocarbon product which is recovered as stream 35. The vapor portion from line 27 passes up through the splitter column 23 to strip CO impurity from the downflowing liquids. The CO enriched vapor stream 28 leaving the top of the splitter column 23 then passes up through the low pressure dephlegmator 29. In low pressure dephlegmator 29, the CO enriched vapor stream is cooled to −157° C. by indirect heat exchange with the high pressure $H_2$—CO vapor stream 18 from the high pressure dephlegmator 16. Essentially all of the $C_1+$ hydrocarbons are recondensed and a high purity, low pressure $H_2$—CO vapor stream 32 containing less than 0.7 mole % $C_1+$ is produced from the overhead of low pressure dephlegmator 29.

As a result of the rectification achieved in low pressure dephlegmator 29, a $C_1+$ enriched liquid stream 30 is produced from the bottom of the dephlegmator, and is combined with the $C_1+$ enriched liquid from line 21 to be passed downward through the column for residual CO removal. The $C_1+$ liquid hydrocarbon product, stream 35, produced from the bottom of the splitter column 23 contains only about 0.1 mole % CO impurity and complies with pipeline specifications for natural gas.

The $C_1+$ hydrocarbon product stream 35 is vaporized in feed cooler 3 and warmed along with the high and low pressure $H_2$—CO streams, 37 and 32 respectively, for refrigeration recovery. Refrigeration for the high pressure dephlegmator 16 is provided by a closed loop $N_2$ recycle stream 14.

A comparison of $H_2$—CO product streams 32 and 37 with feed stream 1 in Table 1 shows that 76% of the product CO and more than 98% of the $H_2$ is recovered at high pressure, essentially feed pressure, with total CO recovery over 99.9%. Recovery of $C_1+$ hydrocarbons in stream 35 is about 97.5%.

At the same product purities and recoveries, a partial condensation process of the prior art would recover only about 27% of the product CO at high pressure, resulting in a two-fold increase in the amount of CO to be separated from the $C_1+$ hydrocarbons and subsequently recompressed to syngas pressure. Additional refrigeration would be required both for the high pressure partial condensation and for conventional low pressure fractionation utilizing an overhead condenser, due to the increased CO loadings. In addition, a portion of the refrigeration would be required at temperatures at least 7° C. colder than the corresponding temperatures in the dual dephlegmator process. As a result, the partial condensation, conventional distillation process of the prior art would require approximately 30% additional energy input.

EXAMPLE 2

A second syngas mixture containing about 58.8 mole % $H_2$, 28.6 mole % CO, 11.8 mole % $C_1$, and 0.8 mole % $N_2$ is also treated in accordance with the above process. The material balance is reported in Table 2 below. The stream numbers refer to the points as represented in FIG. 1.

TABLE 2

| Stream number | 1 | 11 | 17 | 18 | 21 | 25 | 27 | 32 | 35 | 37 |
|---|---|---|---|---|---|---|---|---|---|---|
| Pressure (atm) | 60.9 | 60.0 | 59.9 | 59.9 | 15.8 | 15.9 | 15.9 | 15.6 | 15.9 | 59.5 |
| Temperature (°C.) | 40 | −140 | −145 | −170 | −154 | −112 | −112 | −160 | −112 | −149 |
| Flow Rates (Moles/hr.) (Vapor) | | | | | | | | | | |
| Hydrogen | 6,352 | 6,352 | — | 6,072 | 253 | — | 0 | 280 | — | 6,072 |
| Carbon Monoxide | 3,090 | 3,090 | — | 1,858 | 316 | — | 1.8 | 1,232 | — | 1,858 |
| Methane | 1,277 | 1,277 | — | 40 | 63 | — | 2,196.0 | 10 | — | 40 |
| Nitrogen | 82 | 82 | — | 58 | 8 | — | 0 | 24 | — | 58 |
| TOTAL | 10,801 | 10,801 | — | 8,028 | 640 | — | 2,197.8 | 1,546 | — | 8,028 |
| Flow Rate (Moles/hr.) (Liquid) | | | | | | | | | | |
| Hydrogen | — | — | 280 | — | 27 | 0 | 0 | — | 0 | — |
| Carbon Monoxide | — | — | 1,232 | — | 916 | 2 | 0.2 | — | 0.2 | — |
| Methane | — | — | 1,237 | — | 1,174 | 3,423 | 1,227.0 | — | 1,227.0 | — |
| Nitrogen | — | — | 24 | — | 16 | 0 | 0 | — | 0 | — |
| TOTAL | — | — | 2,773 | — | 2,133 | 3,425 | 1,227.2 | — | 1,227.2 | — |

In this example, a high pressure feed stream 1, at 40° C. and 60.9 atm, is cooled to −140° C., just above its dewpoint, in feed cooler 3. The feed is further cooled to −170° C. in high pressure dephlegmator 16 to produce, via rectification, a high pressure $C_1$ enriched liquid stream 17 containing 45 mole % $C_1$ at −145° C. and a high pressure $H_2$—CO gaseous product stream 18 containing about 0.5 mole % $C_1$.

The high pressure $C_1$ enriched liquid stream 17 is expanded via valve 19 to 15.8 atm and −154° C. and enters the CO—$C_1$ splitter column 23. This liquid, combined with $C_1$ enriched liquid stream 30 from the bottom of the low pressure dephlegmator 29, flows down the column and is partially vaporized in reboiler 7. The vapor-liquid stream from line 27 at −112° C. is separated to provide vapor flow for stripping column 23 and a high purity $C_1$ liquid product stream 35.

The vapor portion from line 27 passes up through the splitter column 23 to strip CO impurity from the downflowing liquids, and then passes up through low pressure dephlegmator 29. The CO enriched vapor is cooled to $-160°$ C. to produce a low pressure $H_2$—CO vapor stream 32 from the overhead of the dephlegmator containing less than 0.7 mole % $C_1$.

As a result of the rectification achieved in low pressure dephlegmator 29, a $C_1$ enriched liquid stream 30 exits the bottom of the dephlegmator 29, and is combined with the $C_1+$ enriched liquid from line 21 to be passed down the column for residual CO removal. The $C_1$ liquid stream 35 produced from the bottom of splitter column 23 contains less than 0.02 mole % CO impurity.

Table 2 shows that 60% of the product CO and over 95% of the $H_2$ are recovered at high pressure, with total $H_2$—CO recovery of essentially 100%. Recovery of $C_1$ is about 96%. At the same product purities and recoveries, a partial condensation process would recover only 19% of the CO at high pressure, resulting in a doubling of the quantity of CO to be separated from $C_1$ via low pressure distillation and subsequently recompressed. The partial condensation/conventional distillation process requires additional refrigeration, some at temperatures 10° C. colder than the dual dephlegmator process, and requires approximately 25% additional energy input.

In both examples presented, it is the high recovery of high purity $H_2$—CO and $C_1+$ hydrocarbon products, combined with significantly reduced energy requirements, which makes the present process uniquely suitable for purification of syngas mixtures prior to subsequent commercial operations.

Having thus described the present invention, what is now deemed appropriate for Letters Patent is set out in the following appended claims.

What is claimed is:

1. A process for separating a high pressure feed gas comprising $H_2$, CO and $C_1+$ hydrocarbons into $H_2$—CO product streams and a $C_1+$ hydrocarbon stream, said process comprising:
   (a) cooling said high pressure feed gas by indirect heat exchange in a high pressure dephlegmator, said feed gas flowing in a generally upward direction to condense and rectify essentially all of the $C_1+$ hydrocarbons, thereby producing a separate high pressure $H_2$—CO vapor stream and a high pressure $C_1+$ enriched liquid stream;
   (b) expanding said high pressure $C_1+$ enriched liquid stream to form a low pressure $C_1+$ enriched liquid stream;
   (c) partially vaporizing the low pressure $C_1+$ enriched liquid stream to form a low pressure vapor stream and a low pressure $C_1+$ liquid product;
   (d) cooling said low pressure vapor stream by indirect heat exchange in a low pressure dephlegmator using the high pressure $H_2$—CO vapor stream from the high pressure dephlegmator as a refrigerant by causing said high pressure $H_2$—CO vapor stream to flow countercurrent to the low pressure vapor stream to condense and rectify essentially all of the $C_1+$ hydrocarbons, thereby producing a separate low pressure $H_2$—CO vapor stream and additional low pressure $C_1+$ liquid product; and
   (e) recovering the high pressure $H_2$—CO vapor stream at a net purity of no more than about 1 mole% of $C_1$ and higher hydrocarbons, the low pressure $H_2$—CO vapor stream at a net purity of no more than about 1 mole% of $C_1$ and higher hydrocarbons, and the low pressure $C_1+$ liquid product.

2. The process in accordance with claim 1 wherein the high pressure feed gas is cooled to near its dew point prior to entering the high pressure dephlegmator.

3. The process in accordance with claim 2 wherein said cooling is provided by passing the high pressure feed gas through a feed cooler.

4. The process in accordance with claim 3 wherein the high pressure feed gas is cooled to a temperature between about $-150°$ to $-190°$ C. in the high pressure dephlegmator.

5. The process in accordance with claim 4 wherein the high pressure $H_2$—CO vapor stream produced in the high pressure dephlegmator contains less than about 1 mole% $C_1+$ hydrocarbons.

6. The process in accordance with claim 5 wherein said low pressure vapor stream is cooled to a temperature between about $-145°$ to $-185°$ C. in the low pressure dephlegmator.

7. The process in accordance with claim 6 wherein greater than 99.9% of the CO present in the high pressure feed is recovered as vapor product.

8. The process in accordance with claim 7 wherein the $H_2$ and CO present in the high presure feed are recovered as vapor products having a combined $H_2$ plus CO purity of greater than 99 mole%.

9. The process in accordance with claim 8 wherein the high pressure $C_1+$ enriched liquid stream produced in the high pressure dephlegmator is expanded to a pressure between about 5 to 20 atmospheres to form a low pressure $C_1+$ enriched liquid stream.

10. The process in accordance with claim 9 wherein greater than 95% of the $C_1+$ hydrocarbons in the high pressure feed are recovered as low pressure $C_1+$ liquid product.

11. The process in accordance with claim 10 wherein the $C_1+$ hydrocarbons in the high pressure feed are recovered at a hydrocarbon purity of greater than about 99.9 mole%.

12. The process in accordance with claim 11 wherein refrigeration for the high pressure dephlegmator is provided by a closed loop $N_2$ recycle system.

13. A process for separating a high pressure feed gas comprising $H_2$, CO and $C_1+$ hydrocarbons into $H_2$—CO product streams and a $C_1+$ hydrocarbon stream, said process comprising:
   (a) cooling said high pressure feed gas by indirect heat exchange in a high pressure dephlegmator, said feed gas flowing in a generally upward direction to condense and rectify essentially all of the $C_1+$ hydrocarbons, thereby producing a separate high pressure $H_2$—CO vapor stream and a high pressure $C_1+$ enriched liquid stream;
   (b) expanding said high pressure $C_1+$ enriched liquid stream to form a low pressure $C_1+$ enriched liquid stream;
   (c) partially vaporizing the low pressure $C_1+$ enriched liquid stream to form a low pressure vapor stream and a low pressure $C_1+$ liquid product;
   (d) cooling said low pressure vapor stream by indirect heat exchange in a low pressure dephlegmator, to condense and rectify essentially all of the $C_1+$ hydrocarbons, thereby producing a separate low pressure $H_2$—CO vapor stream and additional low pressure $C_1+$ liquid product; and (e) recovering the high pressure $H_2$—CO vapor stream at a net purity of no more than about 1 mole% of $C_1$ and higher hydrocarbons, the low pressure $H_2$—CO vapor stream at a net purity of no more than about 1 mole% of $C_1$ and higher hydrocarbons, and the low pressure $C_1+$ liquid product.

14. The process in accordance with claim 13 wherein the high pressure feed gas is cooled to near its dew point prior to entering the high pressure dephlegmator.

15. The process in accordance with claim 14 wherein said cooling is provided by passing the high pressure feed gas through a feed cooler.

16. The process in accordance with claim 15 wherein the high pressure feed gas is cooled to a temperature between about $-150°$ to $-190°$ C. in the high pressure dephlegmator.

17. The process in accordance with claim 16 wherein the high pressure $H_2$—CO vapor stream produced in the high pressure dephlegmator contains less than about 1 mole% $C_1+$ hydrocarbons.

18. The process in accordance with claim 17 wherein said low pressure vapor stream is cooled to a temperature between about $-145°$ to $-185°$ C. in the low pressure dephlegmator.

19. The process in accordance with claim 18 wherein greater than 99.9% of the CO present in the high pressure feed is recovered as vapor product.

20. The process in accordance with claim 19 wherein the $H_2$ and CO present in the high pressure feed are recovered as vapor products having a combined $H_2$ plus CO purity of greater than 99 mole%.

21. The process in accordance with claim 20 wherein the high pressure $C_1+$ enriched liquid stream produced in the high pressure dephlegmator is expanded to a pressure between about 5 to 20 atmospheres to form a low pressure $C_1+$ enriched liquid stream.

22. The process in accordance with claim 21 wherein greater than 95% of the $C_1+$ hydrocarbons in the high pressure feed are recovered as low pressure $C_1+$ liquid product.

23. The process in accordance with claim 22 wherein the $C_1+$ hydrocarbons in the high pressure feed are recovered at a hydrocarbon purity of greater than about 99.9 mole%.

24. The process in accordance with claim 23 wherein refrigeration for the high pressure dephlegmator is provided by a closed loop $N_2$ recycle system.

* * * * *